(12) United States Patent
Bavendiek (10) Patent No.: US 9,372,270 B2
(45) Date of Patent: Jun. 21, 2016

(54) X-RAY LINE DETECTOR AND METHOD FOR THE PRODUCTION THEREOF (71) Applicant: YXLON International GmbH, Hamburg (DE)

(72) Inventor: Klaus Bavendiek, Norderstedt (DE)

(73) Assignee: YXLON International GmbH, Hamburg (DE)

(*) Notice: Subject to any disclaimer, the term of this patent is extended or adjusted under 35 U.S.C. 154(b) by 38 days.

(21) Appl. No.: 14/165,608

(22) Filed: Jan. 28, 2014

(65) Prior Publication Data

US 2014/0197319 A1    Jul. 17, 2014

Related U.S. Application Data (63) Continuation of application No. 13/993,742, filed as application No. PCT/EP2011/006260 on Dec. 12, 2011, now abandoned.

(30) Foreign Application Priority Data

Dec. 13, 2010  (DE) .......................... 10 2010 054 340

(51) Int. Cl.
| G01T 1/20 | (2006.01) |
| A61B 6/00 | (2006.01) |
| A61B 6/03 | (2006.01) |
| G01T 1/29 | (2006.01) |
| H01L 27/146 | (2006.01) |

(52) U.S. Cl.
CPC ............... *G01T 1/2018* (2013.01); *A61B 6/035* (2013.01); *A61B 6/4411* (2013.01); *G01T 1/2985* (2013.01); *H01L 27/14603* (2013.01); *Y10T 29/49002* (2015.01)

(58) Field of Classification Search
CPC .... G01T 1/2018; G01T 1/2985; A61B 6/035; A61B 6/4411; H01L 27/14603; Y10T 29/49002
See application file for complete search history.

(56) References Cited

U.S. PATENT DOCUMENTS

| 4,415,808 | A | * | 11/1983 | Cusano et al. ................. 250/367 |
| 5,148,595 | A | * | 9/1992 | Doggett et al. ................. 29/840 |
| 7,358,501 | B2 | | 4/2008 | Danzer et al. |
| 2006/0054832 | A1 | | 3/2006 | Cambensi et al. |

(Continued)

FOREIGN PATENT DOCUMENTS

| DE | 3825703 A1 | 2/1990 |
| DE | 102004044901 A1 | 3/2006 |

(Continued)

*Primary Examiner* — David Porta
*Assistant Examiner* — Jeremy S Valentiner
(74) *Attorney, Agent, or Firm* — Leydig, Voit & Mayer, Ltd.

(57) ABSTRACT

An X-ray line detector includes a housing and a predefined number of carrier modules having the same width disposed in the housing. A one-piece printed circuit board, on which a photodiode is arranged, is attached to each carrier module. Each printed circuit board is wider than an active area of pixels constituting the photodiode and a scintillator element is attached to each photodiode. Each scintillator element has a length that exactly covers the active area in the width thereof plus an interspace between two adjacent pixels of a photodiode. The width of each carrier module is at most twice as great as the length of a scintillator element. The carrier modules are arranged in two rows in the housing such that the photodiodes of each row are opposite each other, the scintillator elements abut against each other upon contact, and mutually contacting scintillator elements are arranged in respectively opposite rows.

14 Claims, 6 Drawing Sheets (56) References Cited

U.S. PATENT DOCUMENTS

2006/0231767 A1* 10/2006 Danzer et al. ............ 250/370.11
2010/0171038 A1* 7/2010 Wirth ............................ 250/366

FOREIGN PATENT DOCUMENTS

| DE | 102005014187 A1 | 10/2006 |
| GB | 2005405 A | 4/1979 |

* cited by examiner

X-RAY LINE DETECTOR AND METHOD FOR THE PRODUCTION THEREOF

CROSS REFERENCE TO RELATED APPLICATIONS

This application is a continuation from U.S. patent application Ser. No. 13/993,742 filed on Jun. 13, 2013 as a national phase under 35 U.S.C. §371 of International Application No. PCT/EP2011/006260, filed on Dec. 12, 2011, which is incorporated by reference herein and which claims benefit to German Patent Application No. DE 10 2010 054 340.3, filed on Dec. 13, 2010. The International Application was published in German on Jun. 21, 2012, as WO 2012/079737 A2 under PCT Article 21 (2).

FIELD

The invention relates to an X-ray line detector having a predefined number of carrier modules, which each have a photodiode and are arranged in a housing. In addition, the invention relates to a method for the production of such an X-ray line detector.

BACKGROUND

In the case of X-ray line detectors, which are used, in particular, for CT procedures, it is not possible, for an equidistant arrangement of the pixels of the photodiodes of the entire line, for the modules with the photodiodes to be arranged flush with each other in a row, since they have edge regions in which no active regions of the photodiodes are formed. If such modules are nevertheless arranged flush with each other in a row, this then results in a distortion in the X-ray image, owing to the lack of equidistance of the pixels of the photodiodes on adjacent modules. This has been accepted to some extent, although it results in artifacts being produced in the image upon reconstruction, rendering image analysis more difficult.

SUMMARY

In an embodiment, the present invention provides an X-ray line detector includes a housing and a predefined number of carrier modules having the same width disposed in the housing. A one-piece printed circuit board, on which a photodiode is arranged, is attached to each carrier module, respectively. Each printed circuit board is wider than an active area of pixels constituting the photodiode. A scintillator element is attached to each photodiode, respectively. Each scintillator element has a length that exactly covers the active area in the width thereof plus an interspace between two adjacent pixels of a photodiode. The width of each carrier module is at most twice as great as the length of a scintillator element. The carrier modules are arranged in two rows in the housing such that the photodiodes of each row are opposite each other such that the scintillator elements abut against each other upon contact and mutually contacting scintillator elements are arranged in respectively opposite rows.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

An aspect of the invention is to provide an X-ray line detector and a production method for same, in which the photodiodes are arranged such that, even in the case of mutually adjoining photodiodes, the transition does not cause the above-described distortions in the X-ray image, without the necessity for an elaborate fine adjustment.

In an embodiment, the present invention provides an X-ray line detector including a scintillator element having a row of scintillator blocks, together with a respectively intermediate opaque layer. Preferably, the width of a scintillator block is equal to the width of an active area of a pixel of the photodiode, and the width of an opaque layer is equal to the distance of the interspaces between the active regions of adjacent pixels of the photodiode. Since the scintillator elements are attached to the photodiodes and in each case exactly cover the width of the active area of the pixels constituting the photodiodes plus an interspace between two adjacent pixels of the photodiode, the pixels of the entire X-ray line detector can be arranged equidistantly in relation to each other over the entire length thereof. This is achieved in that the carrier modules are arranged in two rows in the housing, wherein a carrier module is always arranged alternately in relation to the next, on the respectively opposite row, and the respective scintillator elements of these mutually opposite carrier modules abut against each other. Since the scintillator elements are exactly the width of the active area of the photodiode plus a distance between two adjacent pixels, it is thus ensured that two mutually adjoining photodiodes adjoin each other without alteration of the distance between the edge pixels of these two photodiodes as compared with the distances of the individual pixels within the diodes. This is possible in that the carrier modules, and therefore also the printed circuit boards arranged thereon, which carry the photodiodes, are at most twice as wide as a scintillator element. It is thereby ensured that the scintillator elements of respectively opposite carrier modules can also actually abut against each other, which would not be possible if the carrier modules were more than twice as wide as the scintillator elements, since then the distance between two scintillator elements of carrier modules that are present on a row and adjoin each other would be greater than the length of the scintillator element. As a result, the edge pixels of mutually adjoining photodiodes would no longer be at the same distance from each other as the pixels inside a photodiode. For the reasons set out further below, it is preferred if the width of each carrier module is as close as possible to twice the length of a scintillator element.

An advantageous development of the invention provides that the housing has a first carrier element and, arranged and formed in mirror symmetry thereto, a second carrier element, between which there is formed an inlet slot for X-ray radiation, wherein the carrier modules are arranged alternately on these two carrier elements and the scintillator elements are arranged in the alignment of the inlet slot. It is thereby ensured that the carrier modules are arranged within the housing in a particularly simple mechanical manner and, moreover, an inlet slot for the X-ray radiation is also created. The spatial arrangement of the inlet slot and scintillator elements is such that the photodiodes are necessarily arranged perpendicularly in relation thereto, on the left and right of the scintillator elements, and consequently only scintillator flashes occurring perpendicularly in relation to the direction of incidence of the X-ray radiation are registered. The X-ray radiation that passes through is then not then incident on the printed circuit boards. A development of the invention, which is described in more detail below, is used in order that X-ray radiation scattered at the scintillator crystal is also not incident on the printed circuit board.

A further development of the invention provides that the carrier elements are formed L-shaped, and formed in each carrier element, respectively, is a groove, which is aligned parallelwise in relation to the inlet slot and in which a lug formed on the carrier modules engages in a form-fit manner. This makes it possible to define two degrees of freedom for the arrangement of the carrier modules on the carrier elements. Consequently, it is only possible to move the carrier modules along the grooves and parallelwise in relation to the inlet slot. This makes it considerably easier to effect fine adjustment of the carrier modules, and therefore of the photodiodes, in relation to each other. For a person skilled in the art, it is quite obvious that an inverse formation is also covered by the invention—i.e. if, formed on each carrier element, there is at least one groove that engages, respectively, at least one lug on the carrier modules that corresponds thereto.

A further advantageous development provides that each carrier module is connected to the respective carrier element by means of at least one fixing element, in particular a fixing screw. This makes it possible, following the high-precision alignment of the individual carrier modules in relation to each other—which is effected by means of the method, described in more detail below, for the production of an X-ray line detector according to the invention—to fix these carrier modules in their position relative to the housing. As a result, it is possible for the scintillator elements, previously subjected to pressure during the assembly of the X-ray line detector, to be relieved again of this pressure.

A further advantageous development of the invention provides that an end plate is arranged, in each case, at the ends of the housing, wherein the first end plate is formed as a stop and the second end plate is formed as a clamping element. As a result, a further degree of freedom is limited, in respect of the arrangement and alignment of the individual carrier modules, and there is the possibility of performing the fine adjustment of the individual carrier modules—and therefore of the photodiodes—in relation to each other by means of the clamping elements.

A further advantageous development of the invention provides that the second end plate has three clamping screws, of which the first clamping screw acts in combination with the first row of carrier modules, the second clamping screw acts in combination with the second row of carrier modules, and the third clamping screw acts in combination with the scintillator elements. The use of clamping screws makes it possible to effect a very fine and secure setting of the spatial relationships between the two rows of carrier modules and the scintillator elements thereof in relation to each other—and therefore of the photodiodes in relation to each other.

A further advantageous development of the invention provides that, on its side opposite the inlet slot, the housing has a cover plate. As a result, the mechanical stability of the X-ray line detector as a whole is increased, since its housing is closed on all sides—apart from the inlet slot. Moreover, harmful environmental influences on the printed circuit boards, for example resulting from soiling, are also prevented, the printed circuit boards being arranged, within the housing, on the carrier modules, and light-tightness is achieved. For this purpose, the inlet slot is also sealed with a metal foil against light and electromagnetic radiation. In addition, the entire housing is also sealed off against air humidity, in order that the scintillator elements do not disintegrate or separate.

Preferably, the cover plate is composed of a material that, for the X-ray radiation energy used, produces scarcely any scattered radiation, in particular it is composed of carbon. By "produces scarcely any scattered radiation" is meant that, in the cover plate, for the energy used (normally $>>100$ keV), a less than 0.1% share of the incident X-ray radiation is absorbed, or scattered. A criterion would be, for example, a low atomic number of $Z<10$. For example, 5 mm of carbon has an approximately 50% absorption at 15 keV; if energies greater than 50 keV are used, more or less all of the X-ray radiation passes through with a negligible proportion of absorption, and consequently a negligible production of scattered radiation.

A further advantageous development of the invention provides that inserted between the first end plate and one of the two rows of carrier modules there is a first buffer piece, which is half as wide as the carrier modules, and inserted between the first end plate and the scintillator elements there is a first spacer, which is half as wide as the scintillator elements. It is thereby ensured that, when the first carrier module abuts against the first end plate, the second carrier module opposite it likewise contacts the end plate by means of the buffer piece, when the two scintillator elements of these two carrier modules contact each other. In order to counteract the pressure of the second scintillator element on the first scintillator element, arranged between the first scintillator element and the first end plate is the buffer piece, which is half as wide and preferably has a low elasticity, such as, for example, hard rubber, in order that, under the pressure of the second scintillator element and the further scintillator elements on the first scintillator element, it can be deformed slightly by the latter. Alternatively, the buffer piece could be composed of metal. It is then formed slightly narrower, and a thin rubber or foam buffer is then additionally attached to the end.

A further advantageous development of the invention provides that inserted between the second end plate and one of the two rows of carrier modules there is a second buffer piece, which is half as wide as the carrier modules, and inserted between the second end plate and the scintillator elements there is a second spacer, which is half as wide as the scintillator elements. As a result, the final carrier modules of each row, which otherwise differ greatly in their distance from the second end plate, and the final scintillator element, located approximately half way therebetween, are at approximately the same distance from the second end plate. As a result, the adjustment of the individual carrier modules in relation to each other can be carried out more easily. Otherwise, in order to be able to achieve this, it would be necessary to use widely differing clamping elements, in particular clamping screws.

A further advantageous development of the invention provides that the printed circuit boards are bent, and electronic components are arranged in the region that, in relation to the photodiode, is formed on the other side of the bend region. As a result—as already indicated briefly above—X-ray radiation that enters the X-ray line detector through the inlet slot and is scattered at the scintillator element cannot be incident on the printed circuit boards in a region in which electronic components are arranged thereon. This prevents damage to or influencing of the electronic components, which react with extreme sensitivity to X-ray radiation.

The object is also achieved by a method having the features of claim 11. Such a production method produces an X-ray line detector that, on the one hand, has extremely exact distances between the edge pixels of adjacent photodiodes, since it is possible to effect an extremely exact mechanical alignment of the carrier modules in relation to each other. On the other hand, this alignment can be achieved in an extremely simple manner by simple mechanical means, wherein this is not dependent on a high accuracy of the printed circuit boards used. The latter can have a relatively large variation in width, since, in respect of mutually contacting scintillator elements (or the photodiodes located beneath them), their width does not affect the distance between the edge pixels of mutually adjoining photodiodes. Since the printed circuit boards, together with the associated carrier module, are at most twice as wide, they are never wider than the greatest distances predefined by the scintillator elements.

An advantageous development of the method provides that subsequently the individual carrier modules are fixed to the housing by means of fixing means, in particular by means of fixing screws, and the third clamping screw is then slackened, such that there is no longer pressure acting on the scintillator elements. It is thereby ensured that the tension on the scintillator elements—which have to be brought into contact with each other under tension—can be removed again following the final adjustment of all carrier modules in relation to each other, since the individual carrier modules are now fixed in their spatial position in relation to the housing, and consequently no more pressure need be exerted on the scintillator elements, as was previously necessary for exact setting of the distance of the photodiodes. This prevents the scintillator elements from breaking off from the photodiodes, to which they are adhesively bonded.

A further advantageous development of the method according to the invention provides that the cover plate is then connected to the housing, in particular by a screwed connection. This achieves—as already described above—a further mechanical stiffening and therefore stabilization of the entire housing, and thus of the X-ray line detector as a whole. Moreover, such an X-ray line detector can also be incorporated "the other way round" into an X-ray inspection installation, such that the X-ray radiation passes in, not through the inlet slot, but from the opposite direction, i.e. through the cover plate. In this case, it is necessary to use a cover-plate material that produces as little scattered radiation as possible, such as, for example, carbon. The necessary inlet slot and the likewise necessary shielding for the electronic components is constituted by a device in front of the cover plate, which device is provided by the user independently of the X-ray line detector, although matched with great precision to the geometry of the latter.

Figure 1A:
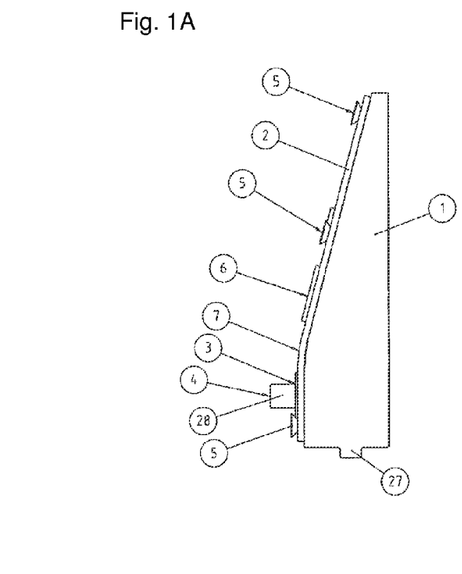
FIGS. 1A, 1B and 1C show a cross section through a carrier module according to the invention and views of a carrier module according to the invention from differing viewing directions.
Figure 1B:
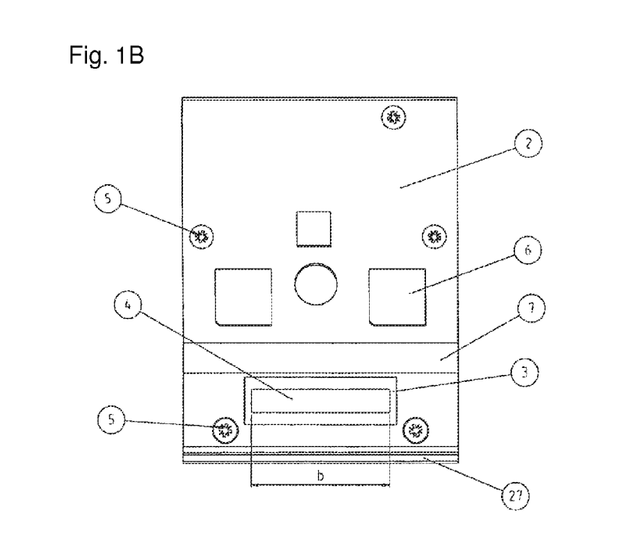
Figure 1C:
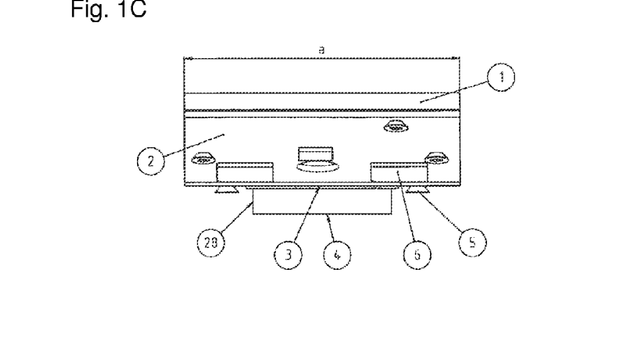

FIG. 1 is composed of three figures, 1A, 1B and 1C, which represent the same component—a carrier module 1—from differing viewing directions, and in a cross section (FIG. 1A).

FIG. 1B shows the carrier module 1 in a view of FIG. 1A from the left, and FIG. 1C shows the carrier module 1 in a top view of FIG. 1A.

It can be seen from FIG. 1A that the cross section of the carrier module 1 is substantially trapezoidal, wherein the upper right tip of the trapezium has been cut away. This tip is constituted by the rear, vertically extending face, and by the obliquely extending face, on which is arranged the bent portion of a printed circuit board 2 that is fitted with electronic components 6. On the surface of the carrier module 1 that is represented on the left in FIG. 1A, the printed circuit board 2 is fixed to the carrier module 1 by means of fastening screws 5. In a lower region that is represented vertically in FIG. 1A, a photodiode 3 is attached to the printed circuit board 2. The photodiode 3 has individual pixels, which each have equal active regions and between which, in each case, there are equidistant spaces.

The printed circuit board 2 extends upwards, via a bend region 7, into an upper region that extends obliquely. Arranged in this upper region are various electronic components 6 such as, for example, a multiplexer and an A/D converter. As a result, it is possible for the light pulses detected by the photodiode 3 to be pre-processed directly on the printed circuit board 2, without intermediately connected long lines, and to be converted into digital signals. This prevents a loss of quality resulting from long analogue lines and interfaces, such as plug connectors.

A scintillator element 4 is adhesively bonded to the photodiode 3. This scintillator element extends horizontally over a length b (see FIG. 1B) that is exactly of such a magnitude that the active region of the photodiode 3, i.e. from the left edge of the left edge pixel to the right edge of the right edge pixel, and, additionally, an interspace between two adjacent pixels within the photodiode 3 is covered. As can be seen from FIG. 1B, the photodiode 3 at the edge also extends beyond the length b of the scintillator element 4, owing to technical production constraints. However, no active surface is contained in this overshooting part, i.e. it does not contain any further pixels of the photodiode 3. The scintillator element 4 serves to convert X-ray radiation, incident from below in FIG. 1A (possibly also from above—more in this connection below), into photons, which are then obliquely or vertically incident on the photodiode 3 and are detected there.

Formed on the lower surface of the carrier module 1 represented in FIG. 1A there is a lug 27, which extends over the entire width a (see FIG. 1C) of the carrier module 1.

The width a of the carrier module 1, or of the printed circuit board 2 attached thereto, is approximately twice as great as the length b of the scintillator element 4. According to the invention, it is necessary that this width a be at most twice the length b of the scintillator element 4, such that the arrangement of all carrier modules 1, represented in FIG. 2, can be realized in an X-ray line detector. At the same time, however, it is advantageous if this width a is approximately twice the length b of the scintillator element 4 in order that, insofar as possible, there can be accommodated on the printed circuit board 2 all electronic components 6 necessary for pre-processing and digitizing there the signals received in the photodiode 3.

According to the invention, the angle in the carrier module 1, within the bend region 7 of the printed circuit board 2, can vary over a wide range. For example, this angle can also be 90°, as shown in the second embodiment example of FIG. 6. It is also quite possible, however, for this angle to be 0°, such that a flat printed circuit board 2 can be used. In this case, the cross section of the carrier module 1 is rectangular. The advantages of a bent printed circuit board 2 are discussed in more detail below in the description relating to FIG. 4.

Figure 2:
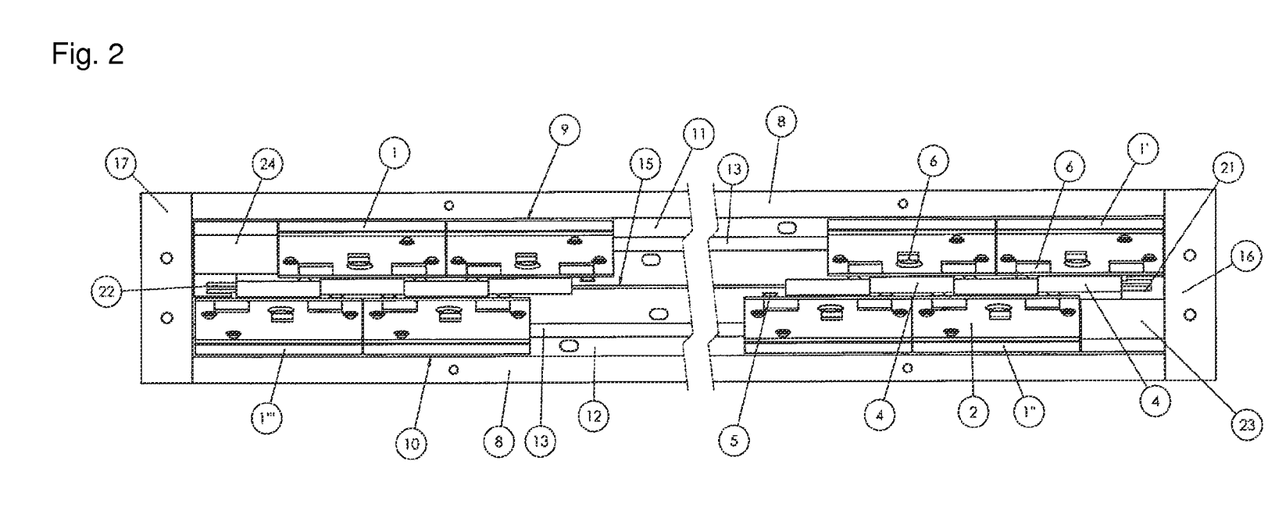
FIG. 2 shows a top view of an assembled X-ray line detector.
Figure 3:
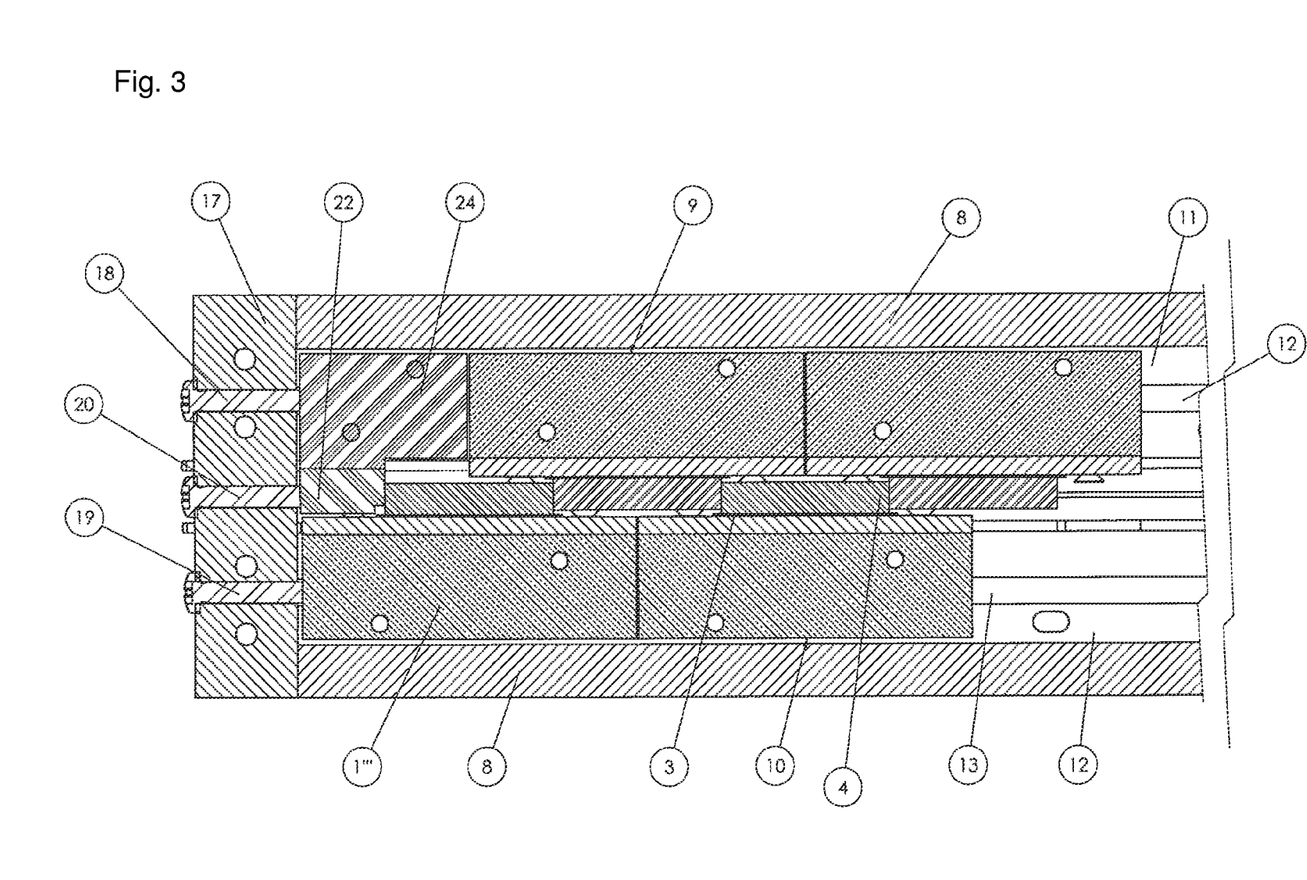
FIG. 3 shows a longitudinal section in a plane that is parallel to the plane shown in FIG. 2.

Represented in FIG. 2, from a viewing direction as in FIG. 1C, i.e. as viewed from above in respect of FIG. 1A, is a complete, fully assembled X-ray line detector having a multiplicity of carrier modules 1. FIG. 3 shows the arrangement in a longitudinal section in a plane extending parallelwise in relation to the plane of drawing of FIG. 2, wherein shown in the region on the left are three clamping screws 18, 19, 20 inside openings in a second end plate 17, which extend through the latter and are therefore not visible in FIG. 2. In the following, FIGS. 2 and 3 are described together, wherein explicit reference is always made only to FIG. 2, unless features can be seen only in FIG. 3—in which case this is stated.

Figure 4:
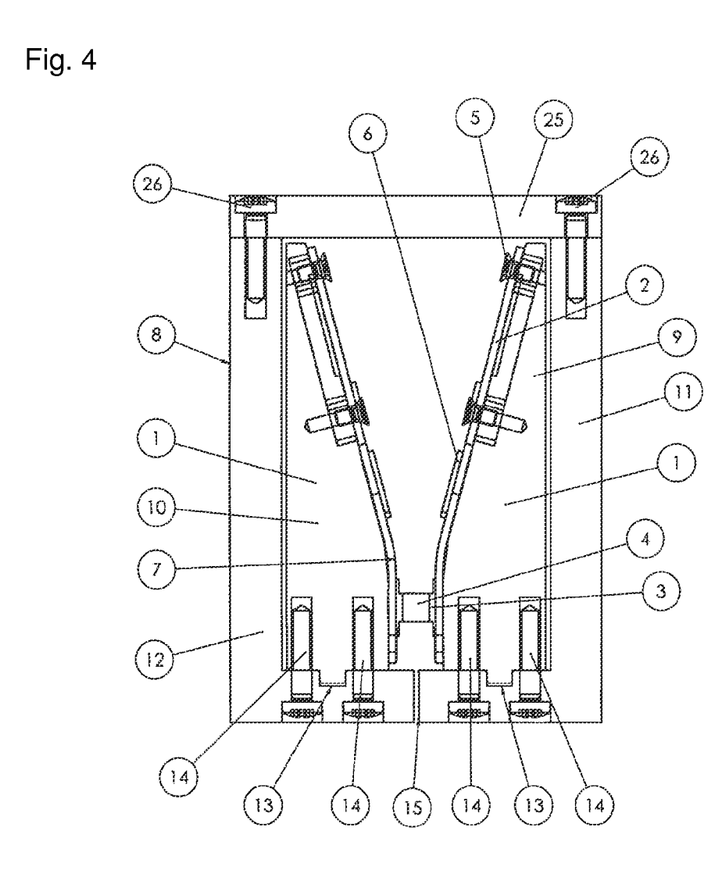
FIG. 4 shows a cross section through the X-ray line detector of FIG. 2, cut in the same direction as FIG. 1A.

The fully assembled X-ray line detector—which is represented in FIG. 4 in cross section as viewed from the same direction as in FIG. 1A—has a housing 8, which serves to accommodate the individual carrier modules 1. In the following, FIGS. 2 to 4 are described together, but generally without specification of which of the figures shows the feature being described in each case.

The housing 8 has a first carrier element 11 and a second carrier element 12, which, in cross section, are each formed substantially L-shaped and arranged in mirror symmetry in relation to a plane of symmetry that, in FIG. 2, is aligned horizontally and is perpendicular to the plane of the page. Formed in the limbs of the two carrier elements 11, 12, which limbs each extend horizontally in FIG. 4, there is a respective groove 13, which extends over the entire length (in FIG. 4 perpendicularly in relation to the plane of the page). This groove 13 is formed so as to be complementary to the lugs 27 (see FIG. 1A) of the carrier modules 1, such that, in FIG. 4, in the vertical and horizontal direction, within the plane of the page, there is a form-fit between these lugs 27 and the grooves 13. A carrier module 1, which is thus inserted in one of these grooves 13, consequently has only one degree of freedom, perpendicularly in relation to the plane of the page, i.e. along the length of the X-ray line detector (this is the horizontal in FIG. 2).

At the two end faces of the housing 8, a first end plate 16 (on the right in FIG. 2) and a second end plate 17 (on the left in FIG. 2) are connected to the two carrier elements 11, 12. Preferably, screwed connections that can be unscrewed are involved here. The dimensions of the two carrier elements 11, 12 and of the two end plates 16, 17 in relation to each other are selected such that an inlet slot 15 is formed between the two horizontally extending limbs of the two carrier elements 11, 12 in FIG. 4. This inlet slot 15 extends over the entire length of the housing 8, from the first end plate 16 to the second end plate 17. The scintillator elements 4 of the individual carrier modules 1 are aligned such that they are arranged upwardly in the alignment of the inlet slot 15 in FIG. 4.

Figure 5:
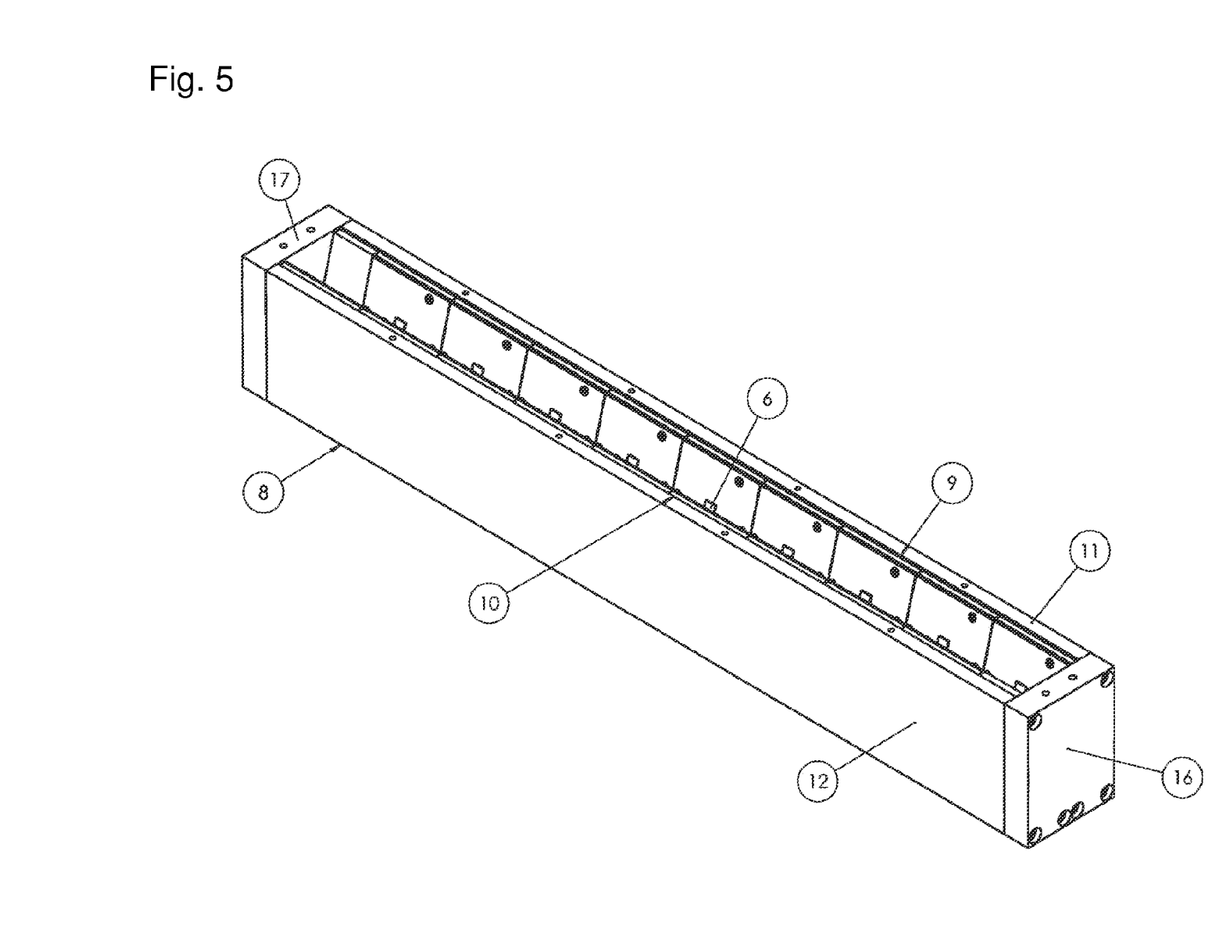
FIG. 5 shows a perspective, oblique top view of the fully assembled X-ray line detector, without a cover plate.

For the purpose of mechanically stabilizing the housing 8 as a whole and, in addition, in order to effect a mechanical and optical barrier against disruptive environmental influences from above, a cover plate 25 is connected, by means of cover screws 26, to the limbs of the L-shaped carrier elements 11, 12 that are represented vertically in FIG. 4; other connection options are equally possible. The cover plate 25 is not represented in FIG. 2, so as to afford a better view of the carrier modules 1 beneath. The same also applies to the perspective, oblique top view of the complete X-ray line detector in FIG. 5, which has been added only to afford a better spatial representation of the entire X-ray line detector in combination with FIGS. 2 to 4.

Within the housing 8, there is a first row 9 of carrier modules 1 placed on the first carrier element 11. A second row 10 of carrier modules 1 is placed on the second carrier element 12 opposite. The carrier modules 1 are all formed alike, wherein their alignment on the two carrier elements 11 and 12 is configured such that they are each aligned with their scintillator element 4 facing towards the other row 9, 10 of carrier modules 1. The arrangement of the carrier modules 1 is such that their scintillator elements 4 abut against each other at the respective end face 28 thereof. This means that a carrier module of the first row 9, because of the two carrier modules 1 of the second row 10 that are arranged in an offset manner in relation to said carrier module of the first row, is always arranged such that one scintillator element 4 is adjacent to another scintillator element 4. The same applies, conversely, to each of the carrier modules 1 of the second row 10 in respect of the carrier modules 1 of the first row 9. It is self-evident that this does not apply to the carrier elements 1', 1''' that are closest to each of the two end plates 16, 17, since these carrier elements have only one partner, offset obliquely thereto, on the respectively other row 9, 10 (see FIG. 2).

Since the width a of the carrier modules 1 and of the printed circuit boards 2 arranged thereon is not quite double the length b of the scintillator elements 4, the carrier modules 1 do not abut against each other in each row 9, 10. In each case, a small interspace is formed between these carrier modules. As shown clearly by FIG. 2, in their parts that project beyond the scintillator elements 4, the photodiodes 3 overlap with the photodiodes 3 located on the respectively other row 9, 10. Since, however, the scintillator elements 4 exactly cover the width of the active areas of the photodiodes 3, i.e. the pixels and, in addition, also the interspace between two adjacent pixels of a photodiode 3, the problems that exist in the state of the art, in particular a distortion in the region between two photodiodes 3, are thus avoided.

Abutting against the first end plate 16 is a first spacer 21, which is aligned in the extension of the end faces 28 of the scintillator elements 4 and consists of a material of low elasticity. The scintillator element 4 of the first carrier module 1' then adjoins this spacer with its one end face 28. Preferably, the length of the first spacer 21 is selected such that there is still a small distance between the first carrier module 1' and the first end plate 16, in order that, during assembly—which is described in more detail below—a slight deformation is rendered possible as a result of the first spacer 21 being compressed in the horizontal direction in FIG. 2, and the first carrier module 1' then contacts the first end plate 16.

A first buffer piece 23 is arranged between the first end plate 16 and the second carrier module 1", which, with its scintillator element 4, contacts the scintillator element 4 of the first carrier module 1' on the left (see FIG. 2). This buffer piece has a length, in the horizontal direction in FIG. 2, that is approximately half the width a of a carrier module 1, i.e. approximately of the same magnitude as the length b of a scintillator element 4. This first buffer piece 23 is also composed of a slightly elastic material such as, for example, hard rubber (similar to the first spacer 21). Alternatively, the first buffer piece 23 can be somewhat narrower and of the same material as the carrier module 1, generally a metal. The lateral play is then provided by a thin rubber buffer.

Arranged at the left end of the X-ray line detector in FIG. 2, in the extension of the scintillator elements 4, is a second spacer 22, which is substantially the same as the first spacer 21. In addition, a second buffer piece 24, formed so as to be substantially the same as the first buffer piece 23, is arranged on the carrier element 11 that is opposite the final carrier module 1'''.

It can be seen in FIG. 3 that acting on the second buffer piece 24 there is a first clamping screw 18, which can be turned towards or away from the first row 9, through a screw hole in the second end plate 17, in the horizontal direction in FIG. 3. Arranged between the final carrier module 1''' of the second row 10 and the second end plate 17 there is a second clamping screw 19, which, likewise, can be turned towards or away from the second row 10, through a screw hole in the second end plate 17. Finally, also present in a further screw hole of the second end plate 17 is a third clamping screw 20, which, by being screwed in, can exert pressure, in the horizontal direction in FIG. 3, on the second spacer 22, and consequently on the row of scintillator elements 4 and, by being screwed out, can relieve pressure therefrom.

It is explained in the following how an X-ray line detector according to the invention, described in more detail above, can be constructed using a method according to the invention.

Firstly, the first spacer 21 is inserted in the housing 8. The first carrier module 1' is then placed, by its lug 27, onto the groove 13 of the first carrier element 11 such that it faces with its scintillator element 4 towards the second carrier element 12. It is pushed towards the first end plate 16 until the end face 28 of its scintillator element 4 contacts the first spacer 21. A first buffer piece 23 is placed onto the second carrier element 12 and brought into contact with the first end plate 16. The second carrier module 1" is then placed onto the second carrier element 12 such that its scintillator element 4 faces towards the first carrier element 11. The second carrier module 1" is moved along the groove 13 towards the first end plate 16 until the end face 28 of its scintillator element 4 contacts the end face 28 of the scintillator element 4 of the first carrier module 1'. The second carrier module 1" is then usually also in contact with the first buffer piece 23.

The sequence specified in the previous paragraph can also be altered such that, following the insertion of the first spacer 21, the first buffer piece 23 is first inserted before the first carrier module 1' and then the second carrier module 1" are inserted, and are each moved as described above. Alternatively, the sequence can also begin with the insertion of the first buffer piece 23 and subsequent insertion of the first spacer 21, and thereafter the first carrier module 1' and then the second carrier module 1" are inserted, and are each moved as described above.

Then, a further carrier module 1, having the same alignment as the first carrier module 1', is placed onto the first carrier element 11 and moved towards the first end plate 16 until the end face 28 of its scintillator element 4 contacts the end face 28 of the scintillator element 4 of the second carrier module 1".

Further carrier modules are then placed, always alternately, onto the second carrier element 12 and the first carrier element 11, wherein the scintillator elements 4 each face towards the opposite carrier module 1 and are then moved as far as possible—i.e. until their own scintillator element 4 comes into contact with the next scintillator element 4—towards the first end plate 16.

After the final carrier module 1''' has been placed on the second carrier element 12—this is not imperative, as it could also be placed on the first carrier element 11—a second buffer piece 24 is placed onto the first carrier element 11, between the second end plate 17 and the final carrier module 1 located on the first carrier element 11. In addition, a second spacer 22 is also arranged, so as to adjoin the end face 28 of the final carrier module 1''', between the latter and the second end plate 17.

Then, a rough adjustment of the carrier modules 1 is done by alternately screwing in the first clamping screw 18 and the second clamping screw 19 in the direction of the first end plate 16, until the final carrier module 1''' comes to be located at a predefined position. This is achieved by a marking on the housing 8 coinciding with a marking on the final carrier module 1'''. This is followed by fine adjustment, in that the third clamping screw 20 is tightened, i.e. screwed-in in the direction of the first end plate 16, until the two above-mentioned markings, on the final carrier module 1''' and on the housing, coincide exactly, wherein all scintillator elements 4 are pressed with the respectively opposite end faces 28 thereof against each other.

In order to prevent the scintillator elements 4, pressed against each other under pressure, from breaking off—this applies, in particular, when the latter have already been exposed to X-ray radiation over a certain period of time, and thus the quality of the adhesive between them and the photodiodes 3 beneath them has deteriorated—load is relieved from the scintillator elements again. This is also advantageous, in particular, during transport of the X-ray detector line. For the purpose of relieving load, the individual carrier modules 1 are fixed to the respective carrier element 11, 12 by at least one associated fixing screw 14 in each case. For this purpose, the respective carrier element 11, 12 has an elongate hole, on its underside in FIG. 4, through which the respective fixing screw 14 can be screwed into a screw hole on the underside of the carrier module 1. Since the individual carrier modules 1 are now fully fixed to the respective carrier element 11, 12, and equidistance between the individual pixels of the photodiodes 3—including in the region of the opposing photodiodes 3 that adjoin each other—is thus ensured, the third clamping screw 20 can be unscrewed again and the pressure on the scintillator elements 4 can thus be removed from the latter. This prevents the scintillator elements from breaking off from the photodiodes 3, or greatly reduces the risk associated therewith.

The two other clamping screws 18, 19 can also be slackened again, since there is no further risk of displacement of the individual carrier modules 1, since the latter have been fixed to the carrier elements 11, 12.

Finally, the cover plate 25 is then fastened, by means of cover screws 26 provided for this purpose, to the side of the housing 8 that is still open at the top (see FIG. 4). This results in a unit that is closed per se, apart from the inlet slot 15 on the underside of the X-ray line detector (as represented in FIG. 4). The slot itself is provided with a thin metal-foil barrier against environmental influences.

The cover plate 25 is composed of a material that produces only a small quantity of (back-scattered) X-ray radiation, such as, for example, carbon.

In order to prevent malfunctions, the carrier modules 1 and the printed circuit boards 2 thereon are provided with a bend region 7, in order that the directly incident X-ray radiation (in FIG. 4, usually entering from below, through the inlet slot 15) and the X-ray radiation scattered at the scintillator elements 4 are not incident on the very sensitive electronic components 6 on the upper part of the printed circuit board 2. This is achieved in that the basic body of the carrier module 1 functions as a shield for the electronic components 6, since scattered radiation, irrespective of which point on the scintillator element 4 it is emitted from, can never be directly incident on the electronic components 6. It is absorbed by the solid body of the carrier module 1.

It must be pointed out in connection with this that the X-ray line detector can also be used "in reverse". This thus means that the X-ray radiation does not enter, from below in FIG. 4, through the inlet slot 15 and generate within the scintillator elements 4 the photons that are then detected in the photodiodes 3, but, instead, in FIG. 4 the X-ray radiation is incident from above, through the cover plate 25. This is used, in particular, in the case of higher-energy X-ray radiation in a range of over 1.5 MeV. In order to ensure, also in the case of this alignment, that, insofar as possible, no scattered radiation is incident on the sensitive electronic components 6, the cover plate 25 must, on the one hand, consist of a material that produces only a very small quantity of scattered radiation, such as, for example, carbon. On the other hand, outside the X-ray line detector there must be a shielding for the X-ray radiation that is otherwise directly incident on the electronic components 6. This shielding (not represented) can also at the same time define the inlet slot, which must be aligned geometrically very accurately to the scintillator elements 4 and the slot 15, in order for the X-ray line detector to work correctly. Owing to the very great mass of this device, it is provided by the user, fixed, as a separate component. The advantage of this direction of radiation is that the majority of the radiation passes through the detector undisturbed and, behind the detector, produces high-energy scattered radiation; the "standard" shielding is dimensioned sufficiently to provide protection against this scattered radiation.

Figure 6:
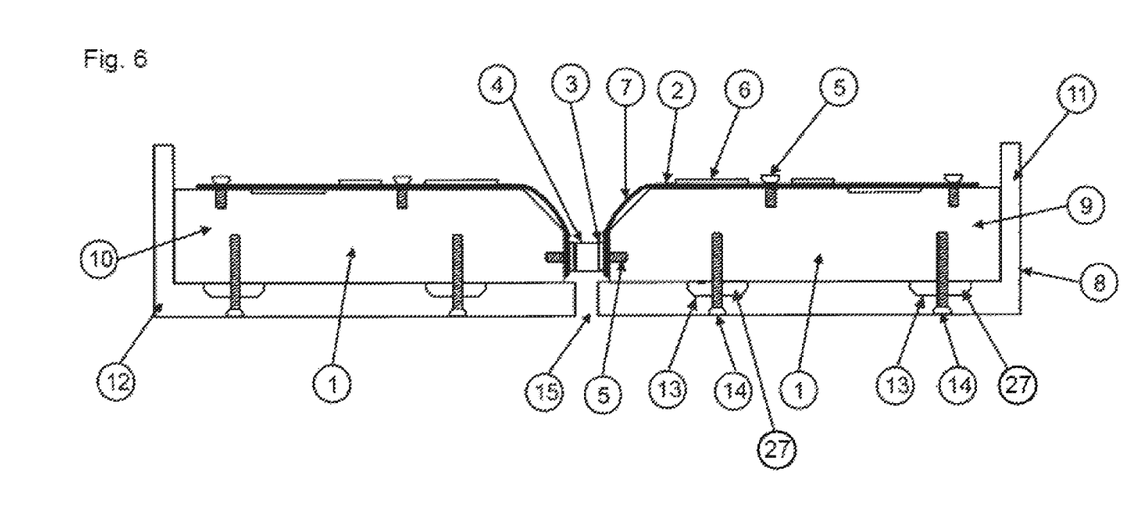
FIG. 6 shows a cross section through a second embodiment example, with a different bend angle of the printed circuit board in a plane like in FIG. 4.

Represented in FIG. 6 is a second embodiment example of an X-ray line detector according to the invention, of which the only fundamental difference, as compared with the first embodiment example described above, is that the bend region 7 has an angle of 90°. This makes it possible for the X-ray line detector as a whole to have a flatter structure, but, logically, it becomes wider as a result (horizontally in FIG. 6). The manner of functioning is exactly as described in relation to the first embodiment example, such that the description is not repeated here. A difference is, in particular, that, owing to the greater bearing surface in the lower region of the carrier modules 1 on the horizontal limbs of the carrier elements 11, 12, two lugs 27 per carrier module 1 are formed in each case, which lugs are then placed in these two associated grooves 13 on the carrier elements 11, 12. To enable better fixing of the carrier modules 1 on the carrier elements 11, 12, fixing screws 14 are then used for each of the two lugs 27.

The view of FIG. 6 corresponds substantially to that of FIG. 4, wherein no cover plate 25 has yet been attached at the upper end of the carrier elements 11, 12.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B." Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise.

LIST OF REFERENCES 1 carrier module
1' first carrier module
1" second carrier module
1''' final carrier module
2 printed circuit board
3 photodiode
4 scintillator element
5 fastening screw
6 electronic component
7 bend region
8 housing
9 first row
10 second row
11 first carrier element
12 second carrier element
13 groove
14 fixing screw
15 inlet slot
16 first end plate
17 second end plate
18 first clamping screw
19 second clamping screw
20 third clamping screw
21 first spacer
22 second spacer
23 first buffer piece
24 second buffer piece
25 cover plate
26 cover screw
27 lug
28 end face
a width of the carrier module
b length of the scintillator element

What is claimed is:

1. An X-ray line detector comprising:
a housing;
a predefined number of carrier modules disposed in the housing, the carrier modules having substantially a same width;
a one-piece printed circuit board, on which a photodiode is arranged, attached to each carrier module, respectively, the printed circuit board being wider than an active area of pixels constituting the photodiode;
a scintillator element attached to each photodiode, respectively, each scintillator element having a length that exactly covers the active area of the respective photodiode in the width thereof and covers an interspace between two adjacent pixels of the respective photodiode, the width of each carrier module being at most twice as great as the length of a scintillator element,
wherein the carrier modules are arranged in a first row and a second row in the housing such that the photodiodes of the first row are opposite the photodiodes of the second row, and such that the scintillator elements of the first row directly abut the scintillator elements of the second row, the scintillator elements being arranged in an alternating manner on the first and second rows.

2. The X-ray line detector according to claim 1, wherein the housing has a first carrier element and a second carrier element disposed and formed in mirror symmetry to the first carrier element, an inlet slot being formed between the first and second carrier elements for X-ray radiation, wherein the carrier modules are arranged alternately on the first and second carrier elements and the scintillator elements are arranged in the alignment of the inlet slot.

3. The X-ray line detector according to claim 2, wherein the carrier elements are L-shaped, and a groove is disposed in each carrier element, respectively, the groove being aligned parallelwise in relation to the inlet slot, and wherein a lug formed on the carrier modules engages the inlet slot in a form-fit manner.

4. The X-ray line detector according to claim 1, wherein each carrier module is connected to the respective carrier element using at least one fixing element.

5. The X-ray line detector according to claim 2, wherein an end plate is arranged at each end of the housing, wherein a first of the end plates is formed as a stop and a second of the end plates is formed as a clamping element.

6. The X-ray line detector according to claim 5, wherein the second end plate has three clamping screws, of which a first of the clamping screws acts in combination with the first row of carrier modules, a second of the clamping screws acts in combination with the second row of carrier modules, and a third of the clamping screws acts in combination with the scintillator elements.

7. The X-ray line detector according to claim 2, wherein the housing includes a cover plate on a side opposite the inlet slot.

8. The X-ray line detector according to claim 7, wherein the cover plate is composed of a material that, for the X-ray radiation energy used, produces scarcely any scattered radiation.

9. The X-ray line detector according to claim 5, wherein a buffer piece is inserted between the end plate and one of the two rows of carrier modules, the buffer piece being half as wide as the carrier modules, and a first spacer is inserted between the first end plate and the scintillator elements, the spacer being half as wide as the scintillator elements.

10. The X-ray line detector according to claim 9, wherein a second buffer piece is inserted between the end plate and one of the two rows of carrier modules, the second buffer plate being half as wide as the carrier modules, and a second spacer inserted between the second end plate and the scintillator elements, the second spacer being half as wide as the scintillator elements.

11. The X-ray line detector according to claim 2, wherein the printed circuit boards are bent so as to produce a bend region, and wherein the respective photodiode is disposed on a first side of the bend region and electronic components are arranged on a second side of the bend region.

12. A method for the production of an X-ray line detector having the features of claim 1, the method comprising:
conducting a first step including one of:
inserting a first spacer on a first end plate and subsequently inserting a first carrier module on the first carrier element until the scintillator element thereof contacts the first spacer, and inserting a first buffer piece on the second carrier element until the first buffer piece contacts the first end plate, wherein the insertion of the first carrier module and the first buffer piece can also be effected in a reverse sequence, or
bringing the first buffer piece on the second carrier element into contact with the first end plate, and bringing the first spacer into contact with the first end plate, and subsequently bringing the first carrier module, with the scintillator element thereof, into contact with the first spacer;
after the first step, inserting a second carrier module such that the scintillator element thereof contacts the scintillator element of the first carrier module and the former itself contacts the first buffer piece;
inserting a carrier module, always alternately, on the first and on the second carrier element, wherein the respective scintillator element thereof contacts the scintillator element of the carrier module inserted directly before it;
in any sequence, bringing a second spacer, which is half as wide as a scintillator element, into contact with the scintillator element of the final carrier module, and bringing a second buffer piece, which is half as wide as a carrier module, into contact with the penultimate inserted carrier module;
actuating a clamping device in the second end plate, so as to press all scintillator elements with the respectively opposite end faces thereof against each other; and
fixing the two rows of carrier modules by means of a clamping device in the second end plate.

13. The method according to claim 12, further comprising fixing the individual carrier to the housing using fixing means such that there is no longer pressure acting on the scintillator elements.

14. The method according to claim 12, further comprising connecting a cover plate to the housing.

* * * * *